(12) United States Patent
Sadatrezaei et al.

(10) Patent No.: US 11,690,840 B2
(45) Date of Patent: Jul. 4, 2023

(54) PHARMACEUTICAL RESINATE COMPOSITIONS AND METHODS OF MAKING AND USING THEREOF

(71) Applicant: RHODES PHARMACEUTICALS L.P., Coventry, RI (US)

(72) Inventors: Mohsen Sadatrezaei, Providence, RI (US); Gerard Frunzi, Garden City, NY (US)

(73) Assignee: Rhodes Pharmaceuticals L.P., Coventry, RI (US)

( * ) Notice: Subject to any disclaimer, the term of this patent is extended or adjusted under 35 U.S.C. 154(b) by 192 days.

(21) Appl. No.: 16/754,940

(22) PCT Filed: Oct. 8, 2018

(86) PCT No.: PCT/US2018/054830
§ 371 (c)(1),
(2) Date: Apr. 9, 2020

(87) PCT Pub. No.: WO2019/074829
PCT Pub. Date: Apr. 18, 2019

(65) Prior Publication Data
US 2020/0253956 A1    Aug. 13, 2020

Related U.S. Application Data

(60) Provisional application No. 62/569,813, filed on Oct. 9, 2017.

(51) Int. Cl.
| | | |
|---|---|---|
| *A61K 31/485* | (2006.01) | |
| *A61K 31/135* | (2006.01) | |
| *A61K 31/167* | (2006.01) | |
| *A61K 31/352* | (2006.01) | |
| *A61K 31/4468* | (2006.01) | |
| *A61K 45/06* | (2006.01) | |
| *A61K 47/34* | (2017.01) | |

(52) U.S. Cl.
CPC .......... *A61K 31/485* (2013.01); *A61K 31/135* (2013.01); *A61K 31/167* (2013.01); *A61K 31/352* (2013.01); *A61K 31/4468* (2013.01); *A61K 45/06* (2013.01); *A61K 47/34* (2013.01)

(58) Field of Classification Search
CPC .. A61K 31/485; A61K 31/135; A61K 31/167; A61K 45/06
See application file for complete search history.

(56) References Cited

U.S. PATENT DOCUMENTS

| | | |
|---|---|---|
| 6,375,957 B1 | 4/2002 | Kaiko et al. |
| 8,883,213 B2 | 11/2014 | Hall et al. |
| 10,350,173 B2 | 7/2019 | Oshlack et al. |
| 2003/0118641 A1 | 6/2003 | Maloney et al. |
| 2004/0091529 A1 | 5/2004 | Edgren et al. |
| 2009/0011027 A1 | 1/2009 | Pathak et al. |
| 2013/0230587 A1 | 9/2013 | Pilgaonkar et al. |
| 2014/0127300 A1 | 5/2014 | Tengler et al. |
| 2014/0127306 A1 | 5/2014 | Mehta et al. |
| 2015/0030677 A1 | 1/2015 | Adjei et al. |
| 2016/0228429 A1 | 8/2016 | Oshlack et al. |

FOREIGN PATENT DOCUMENTS

| | | | |
|---|---|---|---|
| JP | S5369822 A | 6/1978 | |
| JP | 2009530298 A | 8/2009 | |
| JP | 2010529040 A | 8/2010 | |
| JP | 2016222730 A | 12/2016 | |
| WO | 2011/063164 A2 | 5/2011 | |
| WO | 2011/107855 | 9/2011 | |
| WO | WO-2012063257 A2 * | 5/2012 | ........... A61K 9/0095 |
| WO | 2013/119231 | 8/2013 | |
| WO | 2016/094751 | 6/2016 | |

OTHER PUBLICATIONS

European search report for Application No. 18866039.3 completed May 31, 2021, 7 pgs.
Sriwongjanya M. et al., "Effect of ion exchange resins on the drug release form matrix tablets," European Journal of Pharmaceutics and Biopharmaceutics, Nov. 1, 1998, pp. 321-327, vol. 46, No. 3, Elsevier Science Publishers B.V., Amsterdam, NL.
International Search Report for International Application No. PCT/US2018/054830 dated Dec. 26, 2018, 2 pgs.
International Search Report for International Application No. PCT/US17/055878 dated Jan. 9, 2018, 2 pgs.
Japanese Office Action for Japanese Patent Application No. 2020-520112, dated Aug. 9, 2022, 8 pages (English Translation Attached).

* cited by examiner

*Primary Examiner* — Kevin E Weddington
(74) *Attorney, Agent, or Firm* — Lowenstein Sandler LLP (57) ABSTRACT

Disclosed herein Eire pharmaceutical compositions having a mixture of at least one active agent, an ion exchange resin, a binder, and a matrix material such that the composition, when administered to a patient in need thereof, provides the patient with a therapeutic effect for at least about 8 hours and related methods. Also disclosed herein are pharmaceutical compositions having a mixture of a drug susceptible to abuse, a non-opioid analgesic and an ion exchange resin, the composition further including at least one gelling agent and related methods.

27 Claims, 5 Drawing Sheets

FIG. 5

PHARMACEUTICAL RESINATE COMPOSITIONS AND METHODS OF MAKING AND USING THEREOF

FIELD

The present disclosure relates to pharmaceutical compositions which are resistant to tampering and abuse.

BACKGROUND

Pharmaceutical products may be subject to abuse. An individual seeking to abuse a pharmaceutical product may tamper with it in order to extract the active agent contained therein and administer the active agent in a more potent form for abuse. For example, a dose of opioid agonist may be more potent when administered parenterally as compared to the same dose administered orally. Methods of tampering with pharmaceutical products containing opioid agonists intended for oral administration may include, as non-limiting examples, crushing the pharmaceutical product or immersing it in solvents (such as, as a non-limiting example, ethanol) to extract the opioid agonist and administer it in a more potent form (such as, as non-limiting examples, a form for nasal or parenteral administration).

Previous attempts to reduce the abuse potential associated with pharmaceutical products containing opioid analgesics have been made. For example, commercially available tablets sold under trade name TALWIN® NX by Sanofi-Winthrop in the United States contain a combination of an amount of pentazocine hydrochloride equivalent to 50 mg base and an amount of naloxone hydrochloride equivalent to 0.5 mg base. When taken orally, the amount of naloxone present in this combination has low activity and minimally interferes with the pharmacologic action of pentazocine. Whey given parenterally, however, this amount of naloxone, has antagonistic action to narcotic analgesics such as pentazocine. Thus, the inclusion of naloxone may curb a form of misuse of pentazocine which may occur the oral dosage form is solubilized and injected (i.e., parenteral misuse). As additional examples of a similar approach, a fixed combination therapy comprising tilidine hydrochloride hemihydrate and naloxone hydrochloride dihydrate is available in Germany (sold under tradename VALORON® N, Goedecke) and a fixed combination of buprenorphine and naloxone is available in New Zealand (sold under tradename TEMGESIC® NX by Reckitt & Colman).

A need continues to exist in the art for pharmaceutical compositions containing a drug susceptible to abuse that are resistant to parenteral and nasal abuse, however. In addition, in the case of opioid analgesics, a need continues to exist for tamper-resistant formulations that do not solely rely upon the inclusion of an antagonist to deter parenteral and nasal abuse.

SUMMARY

In at least one embodiment, the present disclosure provides a tamper-resistant pharmaceutical composition comprising at least one active agent.

In at least one embodiment, the present disclosure provides a pharmaceutical composition comprising at least one active agent which is less susceptible to parenteral abuse than other pharmaceutical compositions.

In at least one embodiment, the present disclosure provides a pharmaceutical composition comprising at least one active agent which is less susceptible intranasal abuse than other pharmaceutical compositions.

In at least one embodiment, the present disclosure provides a pharmaceutical composition comprising at least one active agent which is less susceptible to diversion than other pharmaceutical compositions.

In at least one embodiment, the present disclosure provides methods of treating a disease or condition in human patients by administering a pharmaceutical composition as disclosed herein to a patient in need thereof.

In at least one embodiment, the present disclosure provides methods of treating pain in human patients by administering to a human patient in need thereof a pharmaceutical composition comprising at least one opioid analgesic while reducing the potential for its abuse.

In at least one embodiment, the present disclosure provides methods of preparing a pharmaceutical composition comprising at least one active agent as disclosed herein.

In at least one embodiment, the present disclosure provides a use of a medicament (e.g., an opioid analgesic) in the manufacture, of a tamper-resistant pharmaceutical composition as disclosed herein for the treatment of a disease state (e.g., pain).

In at least one embodiment, the present disclosure provides a pharmaceutical composition comprising a mixture comprising a complex of at least one active agent and an ion exchange resin, a binder, and a matrix material wherein the composition, when administered to a patient in need thereof, provides the patient with a therapeutic effect for at least about 8 hours, or at least about 12 hours, or at least about 24 hours.

In at least one embodiment, the present disclosure provides a pharmaceutical composition comprising a mixture comprising (i) an admixture f at least one active agent and an ion exchange resin, (ii) a binder, and (iii) a matrix material, wherein the composition, when administered to a patient in need thereof, provides the patient with a therapeutic effect for at least about 8 hours, or at least about 12 hours, or at least about 24 hours.

In at least one embodiment, the present disclosure is directed to methods of treating a disease or condition, such as, as non-limiting examples, pain or attention deficit hyperactivity disorder (ADHD), comprising administering to a patient in need thereof a pharmaceutical composition comprising a mixture of a complex of at least one active agent and an ion exchange resin, a binder, and a matrix material wherein the composition, when administered to a patient in need thereof, provides the patient with a therapeutic effect or a least about 8 hours, or at least about 12 hours, or at least about 24 hours.

In at least one embodiment, the present disclosure provides methods of treating a disease or condition, such as, as non-limiting examples, pain or attention deficit hyperacm disorder (ADHD), comprising administering to a patient in need thereof a pharmaceutical composition comprising a mixture comprising (i) an admixture of at least one active agent and an ion exchange resin, binder, and (iii) a matrix material, wherein the composition, when administered to a patient in need thereof, provides the patient with a therapeutic effect for at least about 8 hours, or at least about 12 hours, or at least about 24 hours.

In at least one embodiment, the present disclosure is directed to methods of deterring abuse of a drug susceptible to abuse, comprising administering to a patient in need thereof a pharmaceutical composition comprising a mixture, comprising a complex of at least one active agent and an ion exchange resin, a binder, and a matrix material, wherein the composition, when administered to a patient in need thereof, provides the patient with a therapeutic effect for at least about 8 hours, or at least about 12 hours, or at least about 24 hours.

In at least one embodiment, the present disclosure is directed to methods of deterring abuse of a drug susceptible to abuse, comprising administering to a patient in need thereof a pharmaceutical composition comprising a mixture, comprising (i) an admixture of at least one active agent and an ion exchange resin, (ii) a binder, and (iii) a matrix material, wherein the composition, when administered to a patient in need thereof, provides the patient with a therapeutic effect for at least about 8 hours, or at least about 12 hours, or at least about 24 hours.

In at least one embodiment, the present disclosure is directed to methods of preparing pharmaceutical compositions comprising forming a complex of at least one active agent and an ion exchange resin, combining the complex with a binder and forming a matrix comprising the complex, the binder, and a matrix material and incorporating the complex into a pharmaceutical composition, wherein the composition, when administered to a patient in need thereof, provides the patient with a therapeutic effect for at least about 8 hours, or at least about 12 hours, or at least about 24 hours.

In at least one embodiment, the present disclosure is directed to methods of preparing pharmaceutical compositions comprising forming a mixture comprising (i) an admixture of at least one active agent and an ion exchange resin, a binder, and (iii) a matrix material and incorporating the complex into a pharmaceutical composition, wherein the composition, when administered to a patient in need thereof, provides the patient with a therapeutic effect for at least about 8 hours, or at least about 12 hours, or at least about 24 hours.

Definitions

In describing the present disclosure, the following terms are to be used as indicated below. As used herein, the singular forms "a," "an," and "the" include plural references unless the context clearly indicates otherwise. Thus, for example, reference to "an active agent" includes a single active agent as well as a mixture of two or more different active agents, and reference to "a resin" includes a single resin as well as a mixture of two or more different resins, and the like.

As used herein, the term about in connection with a measured quantity, refers to the normal variations in that measured quantity, as expected by one of ordinary skill in the art in making the measurement and exercising a level of care commensurate with the objective of measurement and the precision of the measuring equipment. In certain embodiments, the term "about" includes the recited number ±10%, such that "about 10" would include from 9 to 11.

The term "at least about" in connection with a measured quantity refers to the normal variations in the measured quantity, as expected by one of ordinary skill in the art in making the measurement and exercising a level of care commensurate with the objective of measurement and precisions of the measuring equipment and any quantities higher than that. In certain embodiments, the term "at least about" includes the recited number minus 10% and any quantity that is higher such that "at least about 10" would include 9 and anything high than 9. This term can also be expressed as "about 10 or more." Similarly, the term "less than about" typically includes the recited number plus 10% and any quantity that is lower such that "less than about 10" would include 11 and anything less than 11, This term can also be expressed as "about 10 or less."

As used herein, the terms "active agent," "active ingredient," "pharmaceutical agent," and refer to any material that is intended to produce a therapeutic, prophylactic, or other intended effect to a patient in need thereof, whether or not approved by a government agency for that purpose. These terms with respect to specific agents include all pharmaceutically active forms of the agent, including the free base form of the agent, and all pharmaceutically acceptable salts, complexes, stereoisomers, crystalline forms, co-crystals, ether, esters, hydrates, solvates, and mixtures thereof, where the form is pharmaceutically active.

The term "admixture," respect to the at least one active agent and the ion with exchange material, means that the two materials are at least partially dispersed within each other in the form of a physical mixture without chemical interaction.

The term "complex" with respect to the at least one active agent and the ion exchange material, means a material or mixture in which the at least one active agent and the ion exchange material chemically interact, such as, as a non-limiting example, via a chemical bond forming between the two materials, e.g., by covalent binding, ionic binding, van der Waals forces. In certain embodiments, 25% or more, 50% or more, 75% or more, 85% or more or 95% or more of the mi Lure comprises a complex of the at least one active agent and the ion exchange resin.

As used herein, the terms "therapeutically effective" refers to the amount of drug or the rate of drug administration needed to produce a desired therapeutic result in a patient.

As used herein, the terms "prophylactically effective" refers to the amount of drug or the rate of drug administration needed to produce a desired prophylactic result.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but the opposite direction.

The term "chiral center" refers to a carbon atom to which four different groups are attached.

The term "racemic" refers to a mixture of enantiomers.

The term "resolution" refers to the separation or concentration or depletion of one of the two enantiomeric forms of a molecule.

The term "patient" means a subject, particularly a human, who has presented a clinical manifestation of a particular symptom or symptoms suggesting the need for treatment, who treated preventatively or prophylactically for a condition, or who has been diagnosed with a condition to be treated. The term "subject" is inclusive of the definition of the term "patient" and does not exclude individuals who are entirely normal in all respects or with respect to a particular condition.

For purposes of this disclosure, "pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "ppm" as used herein means "parts per million."

The term "layered" means being completely or partially coated onto a substrate.

The term "bioavailability" means to the relevant extent to which the drug (e.g., oxycodone) is absorbed from the unit dosage forms/pharmaceutical compositions. Bioavailability also refers to the AUC (i.e., area under the plasma concentration/time curve).

The term "$C_{max}$" denotes the maximum plasma concentration obtained during the dosing interval.

The term "$T_{max}$" denotes the time to maximum plasma concentration ($C_{max}$).

The terms "population of patients," "population of subjects," and "population of healthy subjects" refer to the mean pharmacokinetic parameters of at least two patients, subjects, or healthy subjects; at least six patients, subjects or healthy subjects; or at least twelve patients, subjects or healthy subjects.

The term "substrate" means a substance or layer of a material. In at least one embodiment, the term "substrate" means an inert core. In at least one embodiment, the term "substrate" means a particle or granule, including, as a non-limiting example, a particle or granule containing an active agent different than or the same as the at least one active agent.

For purposes of the present disclosure, the formulations disclosed herein may be dose proportional. In dose proportional formulations, the pharmacokinetic parameters (e.g., AUC and $C_{max}$) and/or in-vitro release increase linearly from one dosage strength to another. Therefore, the pharmacokinetic and in-vitro parameters of a particular dose can be inferred from the parameters of a different dose of the same formulation.

As used herein, the term "high molecular weight" means an approximate molecular weight of at least 1,000,000 Da. The approximate molecular weight is based on a rheology method to obtain the rheological properties of a compound. For example, polyethylene oxide has an approximate molecular weight of 1,000,000 Da when a 2% (by weight) aqueous solution of the polyethylene oxide, as measured by a Brookfield viscometer Model RVF, spindle No. 1, at 10 rpm, at 25° C., shows a viscosity range of 400 to 800 mPa·s (cP). Polyethylene oxide has an approximate molecular weight of 2,000,000 Da when a 2% (by weight) aqueous solution of the polyethylene oxide, as measured by a Brookfield viscometer Model RVF, spindle No. 3, at 10 rpm, at 25° C., shows a viscosity range of 2000 to 4000 mPa s (cP). Polyethylene oxide has an approximate molecular weight of 4,000,000 Da when a 1% (by weight) aqueous solution of the polyethylene oxide, as measured by a Brookfield viscometer Model RVF, spindle No. 2 at 2 rpm, at 25° C., shows a viscosity range of 1650 to 5500 mPa s (cP). Polyethylene oxide has an approximate molecular weight of 5,000,000 Da when a 1% (by weight) aqueous solution of the polyethylene oxide, as measured by a Brookfield viscometer Model RVF, spindle No. 2, at 2 rpm, at 25° C., shows a viscosity range of 5500 to 7500 mPa s (cP). Polyethylene oxide has an approximate molecular weight of 7,000,000 Da when a 1% (by weight) aqueous solution of said polyethylene oxide, as measured by a Brookfield viscometer Model RVF, spindle No. 2, at 2 rpm, at 25° C., shows a viscosity range of 7500 to 10,000 mPa s (cP). Polyethylene oxide has an approximate molecular weight of 8,000,000 Da when a 1% (by weight) aqueous solution of the polyethylene oxide, as measured by a Brookfield viscometer Model RVF, spindle No. 2, at 2 rpm, at 25° C., shows a viscosity range of 10,000 to 15,000 mPa s (cP). The same rheology methods described above or other rheology methods known to those of ordinary skill in the art be used to determine the molecular weight of other compounds including, but not limited molecular weight hydroxypropylmethylcellulose, high molecular weight hydroxypropylcellulose and high molecular weight ethylcellulose.

The term "low molecular weight" means having, based on the rheology methods described above, an approximate molecular weight of less than 1,000,000 Da. For example, polyethylene oxide has an approximate molecular weight of 100,000 Da when a 5% (by weight) aqueous solution of the polyethylene oxide, as measured by a Brookfield viscometer Model RVT, spindle No. 1, at 50 rpm, at 25° C., shows a viscosity range of 30 to 50 mPa s (cP). Polyethylene oxide has an approximate molecular weight of 900,000 Da when a 5% (by weight) aqueous solution of the polyethylene oxide, as measured by a Brookfield viscometer Model RVF, spindle No. 2, at 2 rpm, at 25° C., shows a viscosity range of 8800 to 17,600 mPa s (cP). The same rheology methods described above or other rheology methods known to those of ordinary skill in the art may be used to determine the molecular weight of other compounds including, but not limited to, low molecular weight hydroxypropylmethylcellulose, low molecular weight hydroxypropylcellulose and low molecular weight ethylcellulose.

DETAILED DESCRIPTION

Pharmaceutical formulations may be the subject of abuse. As one example of a method used to abuse pharmaceutical formulations, a pharmaceutical composition in solid dosage form is crushed in order to liberate the active agent contained therein and administer it, such as through parenteral administration or nasal administration (absorption across a mucosal surface), in a more potent form. As another example, a pharmaceutical composition is dissolved (e.g., in an aqueous or non-aqueous solvent) to make a solution of the active agent that can be readily drawn into a syringe for parenteral administration.

Controlled-release dosage forms play a role in the management of both acute and chronic conditions (e.g., pain management with opioid analgesics). Therefore, tamper-resistant pharmaceutical compositions of drugs susceptible to abuse can maintain a controlled-release profile when administered orally as prescribed.

In at least one embodiment, the present disclosure provides pharmaceutical compositions comprising at least one active agent, an ion exchange material, a binder, and a matrix material which provides a controlled release of the at least one active agent when orally administered as prescribed, but which exhibits decreased dissolution of the at least one active agent when placed in a medium that does not mi gastric fluid, e.g., an aqueous medium (e.g., water) or an alcohol, mixed alcohol, or a mixed alcohol/water medium. In such at least one embodiment, the at least one active agent and the ion exchange material form a complex such that the complex releases the at least one active agent at different rates upon exposure to different media. In another such at least one embodiment, the pharmaceutical composition comprises an admixture of at least one active agent and the ion exchange material, such that the at least one active agent and the ion exchange material form such a complex when the pharmaceutical composition is placed in medium that does not mimic gastric fluid. In particular embodiments, the present compositions exhibit decreased dissolution of the at least one active agent at a pH above about 4.5, above about 5.5 or above about 6.5.

The present disclosure thus provides pharmaceutical compositions comprising a complex or an admixture of at least one active agent and an ion exchange material, wherein the composition, when administered to a patient need thereof, provides the patient with a therapeutic effect for at least about 8 hours, or at least about 12 hours, or at least about 24 hours. In certain embodiments, the composition releases about 10% to about 45% active agent after 1 hour, about 12.5% to about 55% (by weight) agent after 2 hours, about 25% to about 65% (by weight) active agent after 4 hours, about 45% to about 85% (by weight) active agent after 6 hours and about 55% to about 95% (by weight) active agent after 8 hours, and optionally about 75% to 100% (by weight) active agent after 12 hours, when measured by in-vitro dissolution in a USP Apparatus 2 (paddle) at about 50 rpm in about 900 nil simulated gastric fluid at about 37° C.

In other embodiments, the pharmaceutical compositions release one or more of (i) less than 10% active at 1 hour, (ii) less than 20% active agent at 2 hours, (iii) less than 25% active agent at 4 hours, (iv) less than 30% active agent at 6 hours, (v) less than 40% active agent at 8 hours and (vi) less than 50% a e a at 12 hours when measured by in-vitro dissolution in a USP Apparatus 2 (paddle) at about 50 rpm in about 900 ml simulated gastric fluid at about 37° C.

When placed in an aqueous medium, however, the pharmaceutical compositions disclosed herein may exhibit decreased dissolution of the at least one active agent. For example, according to at least one embodiment, the pharmaceutical compositions disclosed herein may In at least one embodiment, the pharmaceutical compositions disclosed herein may release about 20% or less, or about 15% or less, or about 10% or less, or about 5% or less of the at least one active agent within about 20 minutes as measured by in-vitro dissolution in a USP Apparatus 2 (paddle) at about 50 rpm in about 900 ml water at about 37° C. In at least one embodiment, the composition may release about 30% or less, or about 20% or less, or about 15% or less of the at least one active agent within about 45 minutes as measured by in-vitro dissolution in a USP Apparatus 2 (paddle) at about 50 rpm in about 900 ml water at about 37° C. In at least one embodiment, the composition releases about 20% or less, or about 15% or less, or about 10% or less, or about 5% or less of the at least one active agent within about 20 minutes as measured by in-vitro dissolution in a USP Apparatus 2 (paddle) at about 50 rpm in about 900 ml 40% ethanol in water v/v at about 37° C. In at least one embodiment, the composition releases about 30% or less, or about 20% or less, or about 15% or less, or about 10% or less of the at least one active agent within about 45 minutes as measured by in vitro dissolution in a USP Apparatus 2 (paddle) at about 50 rpm in about 900 ml in 40% ethanol in water v/v at about 37° C.

Similarly, the pharmaceutical compositions disclosed herein may exhibit decreased dissolution of the at least one active agent when placed in an alcohol or mixed aqueous/alcohol medium. For example, the pharmaceutical compositions disclosed herein may release about 20% or less, about 10% or less, or about 5% or less of the at least one active agent within about 20 minutes as measured by in-vitro dissolution in a USP Apparatus 2 (paddle) at about 50 rpm in about 900 ml of about 40% alcohol in water (v/v) at about 37° C. In certain embodiments, the composition may release about 30% or less, about 20% or less, or about 10% or less of the active agent within about 45 minutes as measured by in-vitro dissolution in a USP Apparatus 2 (paddle) at about 50 rpm in about 900 ml of about 40% alcohol in water (v/v) at about 37° C. A non-limiting example of an alcohol is ethanol.

This decreased dissolution of the at least one active agent in the pharmaceutical compositions disclosed herein when placed in aqueous media may be measured in terms of "syringeability." For purposes of the present disclosure, "syringeability" refers to the amount of the at least one active agent which may be extracted into a syringe of a particular gauge (e.g., 21G, 23G, 25G, 27G, 28G, 29G, 30G, 31G, etc.) through a cotton ball or other filter material from a mixture of the pharmaceutical composition and a solvent, relative to the total amount of the at least one active agent originally present in the pharmaceutical composition. Non-limiting examples of aqueous media may be useful as solvents to test syringeability include 40% ethanol in water, saline, tap water, and vinegar, for instance. For example, the pharmaceutical composition may be intact, crushed or milled and dissolved in a small amount of solvent (e.g., 1 ml, 5 ml or 10 ml). The dissolution may take place with or without agitation (e.g., vigorous shaking, sonication, etc.) for a particular time period (e.g., 1 min, 5 min or 10 min). The solvent may be at room temperature or boiling, for example. In at least one embodiment, the percent of the at least one active agent extracted into a syringe from a mixture of a pharmaceutical composition as disclosed herein and an aqueous solvent may be about 30% or less, relative to the total amount of the at least one active present in the pharmaceutical composition. In at least one embodiment, for example the percent extracted may be about 29% or less, about 28% or less, about 27% or less, about 26% or less, about 25% or less, about 24% or less, about 23% or less, about 22% or less, about 21% or less, about 20% or less, about 19% or less, about 18% or less, about 17% or less, about 16% or less, about 15% or less, about 14% or less, about 13% or less, about 12% or less, about 11% or less, about 10% or less, about 9% of less, about 8% or less, about 7% or less, about 6% or less, about 5% or less, about 4% or less, about 3% or less, about 2% or less, or about 1% or less.

Ion Exchange Materials

Ion exchange materials suitable for the pharmaceutical compositions disclosed herein are chosen from pharmaceutically acceptable ion exchange materials capable of associating or chemically interacting with at least one active agent either in solution or in situ to form a complex, such as a resinate, and releasing the at least one active agent when the complex is exposed to a release medium. Pharmaceutically acceptable ion exchange materials include any ion exchange material that is not toxic to animals such as humans, does interfere substantially with the medicinal effect of an active agent associated with the ion exchange material, contains a pharmacologically inert matrix containing functional groups that are ionic or that are ionizable under certain conditions of pH, have a moisture content between 0% and the water retention capacity of the ion exchange material, and is minimally soluble or insoluble in water. In at least one embodiment, the ion exchange material, such as a resin, may be a macroporous or gel type resin. In general, ion exchange materials such as resins suitable for use in ion exchange chromatography or for applications such as deionization of water are suitable ion exchange materials in the pharmaceutical compositions disclosed herein. Examples of ion exchange materials, including resins, are described by H. F. Walton in "Principles of Ion Exchange" (pp. 312-343) and "Techniques and Applications of ion-Exchange Chromatography" (pp. 344-361) in Chromatography. (E. Heftmarm, editor), Van Nostrand Reinhold Company, New York (1975); Kitagawa, U.S. Pat. No. 6,218,440; Barhy, U.S. Pat. No. 4,522,953; Dowex: Ion Exchange Resins. Fundamentals of Ion Exchange (2000); and Hughes, Ion Exchange Resins; Unique Solutions to Formulation Problems, Pharmaceutical Technology; Excipients and Solid Dosage Forms, pages 20-25 (June 2004). Examples of ion exchange materials other than resins are described in Hollenbeck, U.S. Patent Publication No. 2005/0013792. Other ion exchange materials, such as cross-linked sodium carboxymethyl cellulose and carbomers, such as those sold under the tradename CARBOPOL® (Noveon Inc Cleveland, Ohio), may also be used. Additional examples of ion exchange materials other than resins are disclosed in Hollenbeck, U.S. Patent Publication No. 2005/0013792.

The ion exchange material or resin can be in an ionized form, a salt form, or a partial salt form, and can be cationic or anionic. Typically, a cationic ion exchange material is used with a positively charged active agent, and an anionic ion exchange material is used with a negatively charged active agent. Non-limiting examples of anionic exchange resins include, but are not limited to, at least one of styrenic, strongly basic anion exchange resins with a quaternary amine functionality; styrenic, weakly basic anion exchange resins with a primary, secondary, or tertiary amine functionality; acrylic or methacrylic strongly basic anion exchange resins with a quaternary amine functionality; acrylic or methacrylic weakly basic anion exchange resins with a primary, secondary, or tertiary amine functionality; and allylic, and vinylic weakly basic anion exchange resins with a primary, secondary, or tertiary amine functionality.

Examples of cationic exchange resins include, but are not limited to, at least one of styrenic, strongly acidic cation exchange resins with sulfonic or phosphonic acid functionality; styrenic, weakly acidic cation exchange resins with carboxylic or phenolic acid functionality; and acrylic or ethacrylic weakly acidic cation exchange resins with a carboxylic or phenolic acid functionality.

According to at least one embodiment, the ion exchange resin can include sulfonated copolymer of styrene and divinylbenzene. In certain embodiments, a suitable ion exchange resin can be the pharmaceutical grade cation exchange resin sold under trade name AMBERLITE™ IRP69 by Dow. Additional non-limiting examples of pharmaceutically acceptable ion exchange materials suitable for the pharmaceutical compositions disclosed herein include those sold under trade names AMBERLITE™ IRP476, AMBERLITE™ IRP64, and AMBERLITE™ IRP88 by Dow.

In at least one embodiment, the ion exchange material may comprise a partial potassium salt of a copolymer of methacrylic acid with divinyl benzene, such as, for example, polacrilin potassium. A non-limiting example of polacrilin potassium includes the product sold under trade name C115KMR by Purolite. Otheriron-limiting examples of pharmaceutically acceptable ion exchange materials suitable for the pharmaceutical compositions disclosed herein include those sold under trade names A430MR, C100CaMR, C100MRNS, C108DR, and C115HMR by Purolite.

In at least one embodiment disclosed herein, the ion exchange material is chosen from polacrilex resin, polacrilin salt, sodium polystyrene sulfonate, cholestyramine resin, and mixtures thereof.

In at least one embodiment disclosed herein, the ion exchange material is chosen from (i) sulfonated copolymers of styrene and divinylbenzene, (ii) methacrylic acid-divinyl benzene copolymers, and (iii) polystyrene resins having amine and/or ammonium side groups.

At Least One Active Agent

The at least one active it in the pharmaceutical compositions disclosed herein may be chosen from, hut not limited to, angiotensin-converting-enzyme (ACE) inhibitors adenohypophoseal hormones, adrenergic neuron blocking agents, adrenocortical steroids, inhibitors of the biosynthesis of adrenoadrenocortical steroids, alpha-adrenergic agonists, alpha-adrenergic antagonists, selectivealpha-two-adrenergic agonists, analgesics, anti-pyretics, anti-inflammatory agents, androgens, local and general anesthetics, anti-addictive agents, anti-androgens, anti-arrhythmic agents, antiasthmatic agents, anti-cholinergic agents, anti-cholinesterase agents, anti-coagulants, anti-diabetic agents, anti-diarrhea agents, anti-diuretic, anti-emetic agents, prokinetic agents, anti-epileptic agents, anti-estrogens, anti-fungal agents, anti-hypertensive agents, anti-microbial agents, anti-migraine agents, anti-muscarinic agents, anti-neoplastic agents, anti-parasitic agents, anti-Parkinson's agents, antiplatelet agents, anti-progestins, anti-schizophrenia agents, anti-thryoid agents, antitussives, anti-viral agents, atypical anti-depressants, azaspirodecanediones, barbiturates, benzodiazepines, benzothiadiazides, beta-adrenergic agonists, betaadrenergic antagonists, selective beta-one-adrenergic antagonists, selective beta-two-adrenergic agonists, bile salts, agents affecting volume and composition of body butyrophenones, agents affecting calcification, calcium channel blockers, cardiovascular drugs, cannabinoids, catecholamines and sympathomimetic drugs, cholinergic agonists, cholinesterase reactivators, central nervous system (CNS) depressants, stimulants, stimulants such as CNS stimulants, contraceptive agents, dermatological agents, diphenylbutylpiperidines, diuretics, ergot alkaloids, estrogens, ganglionic blocking agents, ganglionic stimulating agents, hydantoins, agents for control of acidity and treatment of peptic ulcers, hernatopoietic agents, histamines, histamine antagonists, hormones, 5-hydroxytryptamine antagonists, drugs for the treatment of hyperlipoproteineinia, hypnotics, sedatives, immunosuppressive agents, laxatives, methylxanthines, monoamine oxidase inhibitors, neuromuscular blocking agents, organic nitrates, opioid agonists, opioid antagonists, pancreatic enzymes, phenothiazines, progestins, prostaglandins, agents for the treatment of psychiatric disorders, psychotropics, retinoids, sedative hypnotics, sodium channel blockers, agents for spasticity and acute muscle spasms, succinimides, testosterones, thioxanthines, thrombolytic agents, thyroid agents, tricyclic antidepressants, inhibitors of tubular transport of organic compounds, tranquilizers, drugs affecting uterine motility, vasodilators, vitamins, and mixtures thereof.

In at least one embodiment, the at least one active agent is a drug susceptible to abuse, such as, for example, an opioid analgesic such as an opioid agonist. Non-limiting examples of opioid agonists include alfentanil, all ylprodine, alphaprodine, anileridine, benzylmorphine, bezitramide, buprenorphine, butorphanol, clonitazene, codeine, desomorphine, dextromoramide, dezocine, dimpromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacyhnorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomrphan, phenazocine, phenoperidine, piminodine, piritramide, proheptazine, promedol, properidine, propiram, propoxyphene, sufentanil tilidine, tramadol, pharmaceutically acceptable salts thereof, and mixtures thereof.

In certain embodiments, the opioid agonist may be selected from codeine, fentanyl, hydromorphone, hydrocodone, oxycodone, dihydrocodeine, dihydro orphine, morphine, tramadol, oxymorphone, pharmaceutically acceptable salts thereof, and mixtures thereof.

In various embodiments, the opioid agonist can be chosen from at least one of oxycodone, oxymorphone, hydrocodone, hydromorphone, morphine, codeine, tramadol, tapentadol, fentanyl, pharmaceutically acceptable salts, hydrates and solvates thereof or mixtures thereof. As non-limiting examples, pharmaceutically acceptable salts of opioid agonists include oxycodone hydrochloride, hydrocodone bitartrate, and hydromorphone hydrochloride.

In at least one embodiment, the at least one active agent comprises an opioid agonist such as oxycodone or pharmaceutically acceptable salt thereof present in an amount of, for example, about 2.5 mg, 5 mg, 7.5 mg, 10 mg, 15 mg, 20 mg, 25 mg, or 30 mg. In at least one embodiment, the at least one active agent comprises hydrocodone bitartrate present in an amount of, for example, 2.5 mg, 5 mg, 7.5 mg, 10 mg and 15 mg.

In at least one embodiment, the at least one active agent s oxycodone hydrochloride, and the oxycodone hydrochloride has a 14-hydroxycodeinone level of less than about 25 ppm less than about 15 ppm, less than 5 about 10 ppm, less than about 5 ppm, less than about 2 ppm, less than about 1 ppm, less than about 0.5 ppm or less than about 0.2.5 ppm. WO 2005/097801 A1, U.S. Pat. No. 7,129,248 B2 and US 2006/0173029 A1 all of which are hereby incorporated by reference, describe a process for preparing oxycodone hydrochloride having low levels of 14-hydroxycodeinone.

In at least one embodiment, the drug susceptible to abuse may be chosen from dronabinol, derivatives thereof and mixtures thereof. As a non-limiting example, the pharmaceutical compositions disclosed herein can comprise natural and synthetic delta-9-tetrahydrocannabinol or any salt, isomer, enantiomer, ester, prodrug, and/or derivative thereof.

In at least one embodiment, the drug susceptible to abuse may be chosen from at least one central nervous system (CNS) stimulant. Non-limiting examples of CNS stimulants include amphetamines, phenidates, CNS depressants, tranquilizers, sedative hypnotics, benzodiazepines, barbiturates, pharmaceutically acceptable salts thereof, and combinations thereof. In at least one embodiment, the at least one active agent may comprise a CNS stimulant or a pharmaceutically acceptable salt, hydrate, or solvate thereof or a mixture thereof. In at least one embodiment, the CNS stimulant comprises at least one amphetamine chosen, for example, from gamma-hydroxybutyrate, dextroamphetamine, dextroamphetamine resin complex, methamphetamine, methylphenidate, sibutramine, methylenedioxymethamphetamine, and pharmaceutically acceptable salts, hydrates, and solvates and mixtures thereof.

In at least one embodiment, the CNS stimulant comprises mixed amphetamines and pharmaceutically acceptable salts, hydrates, and solvates, and mixtures thereof. The mixed amphetamines may include at least one of dextroamphetamine saccharate, amphetamine aspartate, dextroamphetamine sulfate and amphetamine sulfate, and pharmaceutically acceptable salts, hydrates, and solvates and mixtures thereof. In at least one embodiment, mixed amphetamine includes pharmaceutically acceptable salts of dextroamphetamine saccharate, amphetamine aspartate, dextroamphetamine sulfate, and amphetamine sulfate.

In at least one embodiment, the CNS stimulant comprises a phenidate, such as, for example, methylphenidate or dexmethylphenidate, and pharmaceutically acceptable salts, hydrates, and solvates and mixtures thereof.

Non-limiting examples of benzodiazepines useful as active agents in the pharmaceutical compositions disclosed herein include alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, and pharmaceutically acceptable salts, hydrates, and solvates and mixtures thereof.

Non-limiting examples of barbiturates useful as active agents in the pharmaceutical compositions disclosed herein include amobarbital, aprobarbotal, butabarbital, butalbital, methohexital, mephobarbital, metharbital, pentobarbital, phenobarbital, secobarbital and pharmaceutically acceptable salts, hydrates, and solvates mixtures thereof.

In at least one embodiment, the pharmaceutical compositions disclosed herein comprise a second active agent, such as a non-opioid. Non-limiting examples of non-opioid analgesics include acetaminophen and non-steroidal anti-inflammatory agents including, but not limited to, aspirin, celecoxib, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indoclidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts, hydrates and solvates thereof and mixtures theicof. In at least one embodiment, the second active agent comprises acetaminophen in the form of granules. A non-limiting example of acetaminophen granules suitable for use in the pharmaceutical compositions disclosed herein are those marketed under trade name COMPRESSO PAP 90 CPF by Granules India.

Alternatively, the second active agent can be an antagonist to the active agent, such as, for example, naltrexone, naloxone, nalmefene, cyclazacine, levallorphan, buprenorphine, pharmaceutically acceptable salts, hydrates and solvates thereof, and mixtures thereof. In at least one embodiment, the antagonist can be an opioid antagonist, non-limiting examples of which include amiphenazole, naltrexone, methylnaltrexone, naloxone, nalbuphine, nalorphine, nalorphine dinicotinate, nalmefene, nadide, levallorphan, cyclozocine, pharmaceutically acceptable salts, hydrates and solvates thereof and mixtures thereof (e naltrexone hydrochloride, naloxone hydrochloride, etc.). In at least one embodiment, the antagonist may be combined with the at least one active agent and the ion exchange material such that the antagonist forms a complex with the ion exchange material, in addition to the complex of the at least one active agent and the ion exchange material.

In pharmaceutical compositions having (1) at least one active agent admixed or complexed with the ion exchange material and (2) a second active agent (such as, for example, pharmaceutical compositions in which the admixture or complex containing the at least one active agent is mixed with or coated on a substrate comprising the second active agent), the first active agent can be an opioid agonist and the second active agent can be a non-opioid analgesic. In at least one such embodiment, the non-opioid analgesic is chosen from, for example, acetaminophen and nonsteroidalnatory agents (e.g., acetaminophen, ibuprofen, aspirin or diclofenac as described herein) and the opioid agonist is chosen from, for example, oxycodone, hydrocodone or pharmaceutically acceptable salts, hydrates or solvates thereof (such as oxycodone hydrochloride or hydrocodone bitartrate).

Binder

The at least one binder in the pharmaceutical compositions disclosed herein may be chosen from, but not limited to, a cellulosic polymer such as hydroxypropylmethylcellulose, hydroxypropylcellulose or hydroxyethylcellulose. The binder can be, for example, a low molecular weight hydroxypropylmethylceliulose, a low molecular weight hydroxypropylcellulose, or a low molecular weight hydroxyethylcellulose. Other binders include, but are not limited to, polyethylene glycol, an acrylic polymer, an acrylic copolymer, a graft copolymer of polyvinyl alcohol and polyethylene glycol, a polyvinyl alcohol, alginic acid, sodium alginate, starch, pregelatinized starch, sucrose, guar gum, salts thereof, derivatives thereof and combinations thereof. In certain embodiments, the pharmaceutical composition may include granules comprising a complex of the at least one active agent and the ion exchange resin, the binder (e.g., a low molecular weight hydroxypropylmethylcellulose) and at least one pharmaceutically acceptable excipient (e.g., a mixture of lactose monohydrate and microcrystalline ellulose), wherein the granules are dispersed in a matrix material (e.g., a high molecular weight hydroxypropylmethylcellulose) According to various embodiments, the binder (e.g., hydroxypropylmethylcellulose) may have a molecular weight about 100 Da to less than 1,000,000 Da, or about 1,000 Da to about 750,000 Da, or about 5,000 Da to about 500,000 Da, or about 10,000 Da to about 100,000 Da, or about 12,000 Da to about 50,0000, or about 16,000 Da to about 20,000 Da, or about 12,000 Da, or about 14,000 Da, or about 16,000 Da, or about 20,000 Da, or about 25,000 Da.

Additional binder materials include, but are not limited to, natural or synthetic waxes, fatty alcohols (e.g., lauryl, myristyl, stearyl, cetyl or cetostearyl alcohol), fatty acids (including, hut not limited to, fatty acid esters and fatty acid glycerides, e.g., mono-, di-, and tri-glycerides), hydrogenated fats, hydrocarbons, stearic acid, hydrophobic and hydrophilic materials having hydrocarbon backbones, acacia, tragacanth, sucrose, gelatin, glucose, cellulose materials (e.g., low molecular weight hydroxypropylmethylcellulose, methylcellulose and sodium carboxymethylcellulose (e.g., Tylose™)), magnesium aluminum silicate, polysaccharide acids, bentonites, polyvinylpyrrolidone (povidone), polymethacrylates and pregelatinized starch (such as National™ 1511 and Starch 1500) and combinations thereof. Suitable waxes include, for example, beeswax, glycowax, castor wax, carnauba wax and other wax-like substances. A "wax-like" substance is defined as any material which is normally solid at room temperature and has a melting point of from about 30° C. to about 100° C. The pharmaceutical compositions according to the disclosure can include one or more binding agents and/or adhesives in the range of about 0.5% to about 25%, or about 0.75% to about 15%, or about 1% to about 10%, of the total weight of the formulation. In certain embodiments of the pharmaceutical composition, a low molecular weight hydroxypropylmethylcellulose is used as the binder. The binder (e.g., a low molecular weight hydroxypropylmethylcellulose) may be present at a range of about 0.5% to about 10%, or about 1% to about 8%, or about 2% to about 4%, of the total weight of the formulation.

Additional examples of binders which may be used include, but are not limited to, digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable natural and synthetic waxes and polyalkylene glycols. In certain embodiments, hydrocarbons having a melting point ranging from about 25° C. to about 90° C. may be included. Of the long-chain hydrocarbon binder materials, fatty (aliphatic) alcohols can be incorporated into the mixture according to certain embodiments. In further embodiments, the mixture or pharmaceutical composition may contain up to 80% (by weight) of at least one digestible, long chain hydrocarbon.

Pharmaceutically Acceptable Excipient

The pharmaceutical composition according to the disclosure can further include one or more pharmaceutically acceptable excipients. Examples of possible pharmaceutically acceptable excipients are described, in the Handbook of Pharmaceutical Excipients, American Pharmaceutical Association, 8th, Ed. (2017), which is incorporated by reference herein. Suitable excipients include, but are not limited to, plasticizers, colorants, lubricants, thermal lubricants, antioxidants, buffering agents, disintegrants or granulating agents, binding agents, diluents, glidants, anti-adherants, sweeteners, chelating agents, granulating agents, bulking agents, flavorants surfactants, solubilizers, stabilizers, hydrophilic polymers, hydrophobic polymers, waxes, lipophilic materials, absorption enhancers, preservative, absorbent, cross-linking agents, bioadhesive polymers, pore formers, osmotic agents, polycarboxylic acids or combinations thereof.

Examples of suitable disintegrants include, but are not limited to, sodium starch glycolate, clays (such as Veegum™ HV), celluloses such as purified cellulose, methylcellulose, sodium carboxymethylcellulose, and carboxymethylcellulose), cross-linked sodium carboxymethylcellulose, starch, cross-linked polyvinylpyrrolidone (e.g., crospovidone), alginates, cornstarches, pre-gelatinized corn starches (such as National™ 1551 and National™ 1550), gums (such as agar, guar, locust bean, pectin, and tragacanth) and mixtures thereof. Disintegrants can be added at any suitable step during the preparation of the pharmaceutical compositions, such as prior to granulation or during a lubrication step prior to compression or encapsulation. The pharmaceutical compositions as described herein can include one or more disintegrants in the range of about 0.5% to about 30%, or about 1% to about 10%, or about 2% to about 6%, of the total weight of the formulation.

Suitable bulking agents includes, but are not limited to, starches (e.g., corn starch), microcrystalline cellulose, lactose (e.g., lactose monohydrate), sucrose, dextrose, mannitol, calcium phosphate and dicalcium phosphate.

According to certain embodiments, the pharmaceutical compositions may include a plasticizer. Plasticizers may interact with hydrophobic materials resulting in a lower viscosity of the mixture as compared to the mixture without the plasticizer when measured under the same conditions. Certain plasticizers may lower the glass transition temperature (Tg) of hydrophobic materials. Suitable plasticizers include, but are not limited to, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol and glycerin. Such plasticizers may include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene, glycol monoethyl ether, sorbitol lactate, ethyl lactate, butyl lactate, ethyl glycolate, dibutyl sebacate, acetyltributylcitrate, triethyl citrate, acetyl triethyl citrate, tributyl city to and allyl glycolate. In certain embodiments, the plasticizer may be in an amount of about or less, or about 4% or less, or about 2% or less, or 0% (i.e., plasticizer free), relative to the total weight of the composition.

In at least one embodiment, the pharmaceutical composition includes a glidant. A glidant is an excipient that improves the flow characteristics of a compressible powder such as tablet ingredients or granules. Suitable glidants include, but are not limited to, silicon dioxide, colloidal silicon dioxide and the like.

Suitable diluents useful in pharmaceutical compositions as described herein include, but are not limited to, lactose (e.g., lactose (anhydrous), lactose (spray dried), lactose monohydrate), starch (e.g., directly compressible starch), mannitol, sorbitol, dextrose monohydrate, microcrystalline cellulose, dibasic calcium phosphate dihydrate, sucrose-based diluents, confectioner's sugar, monobasic calcium sulfate monohydrate, calcium sulfate dihydrate, calcium lactate trihydrate granular, dextrates (e.g., Emdex™), dextrose (e.g., Cerelose™), inositol, hydrolyzed cereal solids such as the Maltrons™ and Mor-Rex™, amylose, powdered cellulose (e.g., Elcema™), calcium carbonate, glycine, bentonite, polyvinylpyrrolidone, and the like. In certain embodiments, the pharmaceutical compositions described herein can include the diluents in the range of about 5% to about 99%, or from about 25% to about 90%, or from about 40% to about 80%, of the total weight of the formulation. Lactose has a melting point of about 202° C. Microcrystalline cellulose has a burning point of over 200° C. before it reaches a melting point, and therefore is also suitable as it does not have a low melting point.

Suitable lubricants include, but are not limited to, glyceryl behenate (Compritol™ 888), metallic stearates (e.g., magnesium, calcium and sodium stearates), stearic acid, hydrogenated vegetable oils (e.g., Sterotex™), talc, waxes such as beeswax and carnauba wax, silica, fumed silica, colloidal silica, calcium stearate, long chain fatty alcohols, boric acid, sodium benzoate, and sodium acetate, sodium chloride, DL-Leucine, polyethylene glycols (e.g., Carbowax™ 4000 and Carbowax™ 6000), sodium oleate, sodium benzoate, sodium acetate, sodium lauryl sulfate, sodium stearyl fumarate (Pruv™), magnesium lauryl sulfate, stearic acid, stearyl alcohol, mineral oil, paraffin, micro crystalline cellulose, glycerin, propylene glycol and combinations thereof. In certain embodiments, the pharmaceutical compositions may include one or more lubricants in an amount of from about 0.1% to about 10%, or from about 0.2% to about 8%, or from about 0.25% to about 5%, of the total weight of the formulation. Magnesium stearate is a lubricant suitable for use in certain embodiments of the pharmaceutical compositions. Magnesium stearate has a melting point of about 90° C. Although magnesium stearate has a low melting point, it can be utilized in small amounts (e.g., about 0.5%) as a lubricant without significantly affecting the stability of the peripheral opioid formulations of the present invention.

Suitable anti-adherents include, but are not limited to, talc, cornstarch, colloidal silicone dioxide (Cab-O-Sil™), DL-Leucine, sodium lauryl sulfate, and metallic stearates. In certain embodiments, the pharmaceutical compositions can include an anti-adherent in an amount from about 0.1% to about 15%, or from about 0.25% to about 10%, or from about 0.5% to about 5%, of the total, weight of the formulation. Colloidal silicon dioxide is an anti-adherent agent suitable for use in some embodiments of the pharmaceutical compositions in an amount from about 0.1% to about 10%, or from about 0.25% to about 5%, or from about 0.5% to about 2%, of the total weight of the formulation. Colloidal silicon dioxide has a melting point of about 1700° C.

Other excipients (such as colorants, flavors and sweeteners) can be utilized in embodiments of the pharmaceutical compositions where they impart little to no deleterious effect on the stability of the pharmaceutical composition.

In certain embodiments, the pharmaceutical composition may include a film coat. The film coat may include, but is not limited to, hydroxypropylmethylcellulose, polyethylene glycol, polyvinyl alcohol or a mixture of any two or more thereof. According to certain embodiments, the film coat may provide a weight gain to the tablet of about 5% or less, or about 4% or less, or about 2% or less.

In certain embodiments, the pharmaceutical composition can further comprise additional materials for deterring abuse such as gelling agents, bittering agents, and/or irritants. As non-limiting examples, the gelling agent may be chosen from sugars, sugar derived alcohols, starch, starch derivatives such as pregelatinized starch, cellulose derivatives, attapulgites, bentonites, dextrins, alginates, carrageenan, gums, pectins, gelatin, kaolin, lecithin, magnesium aluminum silicate, carbomers, carbopols, polyvinylpyrrolidone, polyethylene glycol, polyethylene oxide, polyvinyl alcohol, silicon dioxide, curdlan, furcelleran, egg white powder, facto albumin, soy protein, chitosan, surfactants such as but not limited to sodium laurel sulfate, emulsifiers, and pharmaceutically acceptable salts thereof and mixtures thereof.

A non-limiting example of a pregelatinized starch suitable for use in the pharmaceutical compositions disclosed herein is the product sold under trade name SWELSTAR MX-1 by Asahi Kasei. A non-limiting example of a gum suitable for use in the pharmaceutical compositions disclosed herein is xanthan gum, such as, for instance, the product sold under trade name XANTURAL 180 by CP Kelco. As non-limiting examples, the bittering agent may be chosen from flavor oils, flavoring aromatics, oleoresins, plant extracts, leaf extracts, flower extracts, fruit extracts, sucrose derivatives, chlorosucrose derivatives, quinine sulphate, denatonium benzoate, and mixtures thereof. As non-limiting examples, the irritant may be chosen from surfactants, capsaicin, capsaicin analogs, and mixtures thereof.

Matrix Material

In various embodiments, the pharmaceutical composition according to the disclosure can include at least one matrix material. Suitable matrix materials may include, but are not limited to, hydrophilic or hydrophobic polymers, such as, e.g., gums, cellulose ethers, cellulose esters, acrylic resins, protein-based materials, nylon, polyvinyl chloride, starch and/or polyvinyl pyrrolidone. Suitable water-soluble polymers include, but are not limited to, polyvinyl pyrrolidone, hydroxypropyl cellulose, hydroxypropylmethyl cellulose, hydroxyethyl cellulose, hydroxymethyl cellulose, polyvinyl alcohols), alginates, polydextrose, carboxymethylene, hydrogenated hydroxyalkyl cellulose and/or hydroxypropylmethyl cellulose ether. Suitable water-insoluble or partially water-insoluble polymers include, but are not limited to, polyvinyl chloride, ethyl cellulose, methyl cellulose, carboxymethyl cellulose, cellulose acetates, cellulose acetate phthalates, ethylene vinyl alcohol, alginic acid and/or its derivatives, acrylic acid and/or methacrylic acid copolymers, methyl methacrylate copolymers, ethoxy ethyl methacrylate copolymers, cyanoethyl methacrylates, aminoalkyl methacrylate copolymers, poly(acrylic acid), poly(methacrylic a methacrylic acid alkylamide copolymers, poly (methyl methacrylates), poly(methacrylic anhydrides), methyl methacrylates, polymethacrylates, poly(methyl methacrylate) copolymer, polyacrylamides, aminoalkyl methacrylate copolymers and/or glycidyl methacrylate copolymers.

Other suitable matrix materials include, but are not limited to, digestible, substituted or unsubstituted long-chain ($C_8$-$C_{50}$, in particular $C_{12}$-$C_{40}$) hydrocarbons such as, e.g., fatty acids, fatty alcohols (lauryl, myristyl, stearyl, cetostearyl, ceryl or cetyl alcohol), glycerol esters of fatty acids (Witepsol, glycerol monostearate), mineral and vegetable oils (hydrogenated castor oil) and/or axes (paraffin waxes, silicone waxes, beeswaxes castor waxes, carnauba waxes and/or Glyco waxes).

According to certain embodiments, the pharmaceutical compositions as described herein may include a high molecular weight hydroxypropylmethylcellulose, a high molecular weight polyethylene oxide, a high molecular weight hydroxyethylcellulose, a high molecular weight hydroxypropylcellulose, a high molecular weight methylcellulose, an alginate, a carbopol (polyacrylic acid), a polymethacrylate, a wax, carnauba wax, beeswax, glycerine alginate (Gelucire®), polyglycolyzed glyceride and combinations thereof. According to various embodiments of pharmaceutical compositions described herein, high molecular weight components molecular weight of at least 1,000,000 Da, or at least 2,000,000 Da, or at least 5,000,000 Da, or at least 7,500,000 Da, or at least 10,000,000 Da, or about 1,000,000 Da to about 10,000,000 Da, or about 2,000,000 Da to about 7,500,000 Da, or about 3,000,000 Da to about 5,000,000 Da. Pharmaceutical compositions as described herein may contain about 1% to about 90% (weight percent) of one or more of the hydrophilic or hydrophobic polymers as a matrix material.

Dosage Forms

The pharmaceutical compositions disclosed herein can be in solid oral dosage form such as a pharmaceutically acceptable tablet or capsule. Typically, mixtures or blends of dried particles or granules containing, for example, (1) the admixture or complex of the at least one active agent and the ion exchange material, (2) the binder, (3) the matrix material and (4) optionally, excipients, are compressed into tablets or encapsulated in pharmaceutically acceptable capsules. Alternatively, mixtures or blends of dried particles or granules may comprise (1) a coating of the admixture or complex and a binder on (2) a substrate, which may or may not comprise the same or a different active agent as the admixture or complex, (3) a matrix material wherein the substrates are dispersed in the matrix material, and (4) optionally, excipients, which may then be compressed into tablets or encapsulated in pharmaceutically acceptable capsules.

The pharmaceutical compositions disclosed herein may comprise controlled release dosage forms prepared using any suitable method known in the art.

Methods of Making

The present disclosure also provides methods of preparing the pharmaceutical composition disclosed herein, comprising (i) combining a least one active agent and an ion exchange material to form an admixture or a complex of the at least one active agent and the ion exchange material, (ii) combining the admixture or complex with a binder, (iii) optionally forming granules from the admixture or complex and the binder, (iv) dispersing the admixture or complex and binder (e.g., as granules) in a matrix material and (iv) incorporating the resulting matrix into a pharmaceutical composition, wherein the composition, when administered to a patient in need thereof, provides the patient with a therapeutic effect for at least about 8 hours, or at least about 2 hours, or at least about 24 hours.

Figure 1:
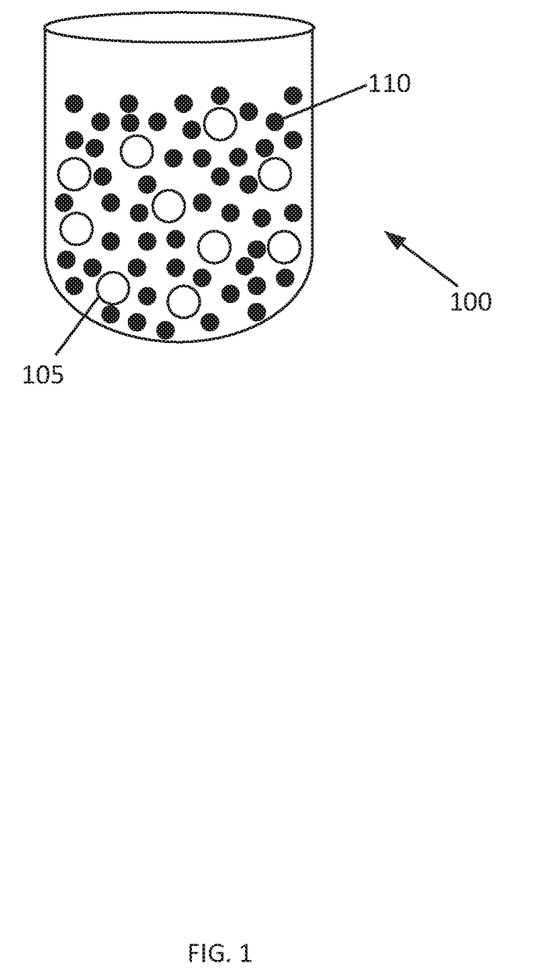
FIG. 1 is a graphical depiction of an exemplary pharmaceutical composition comprising arm admixture of at least one active agent and an ion exchange material, formed in the absence of an aqueous medium, according to an exemplary embodiment of the present disclosure.
Figure 2:
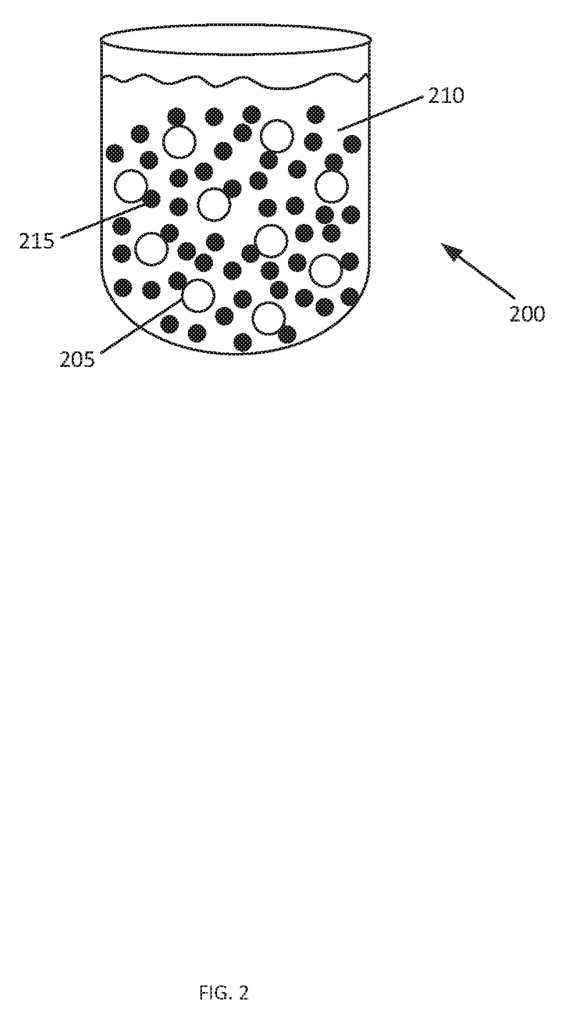
FIG. 2 is a graphical depiction of a pharmaceutical composition comprising a complex of at least one active agent and an ion exchange material, form in the presence of an aqueous medium, according to an exemplary embodiment of the present disclosure.

Referring to FIGS. 1 and 2, according to various embodiments, the present disclosure provides pharmaceutical compositions, such as tablets and capsules, wherein (a) an admixture 100 of at least one active agent 105 and ion exchange resin 110 is formed in the absence of an aqueous medium or (b) a complex 200 of at least one active agent 205 and ion exchange resin 215 is formed in the presence of an aqueous medium 210.

As such, in at least one embodiment, the methods of preparing the pharmaceutical compositions disclosed herein comprise (i) preparing an aqueous mixture by combining the at least one active agent, the ion exchange material, a binder and an aqueous medium; and (ii) drying the aqueous mixture. The at least one active agent, the ion exchange material, the binder and the aqueous medium can be combined in any order. In certain embodiments, however, preparing the aqueous mixture comprises (i) preparing a solution of the active agent in the aqueous medium (ii) adding the ion exchange material to the solution, and (iii) adding the binder to the solution.

Figure 3:
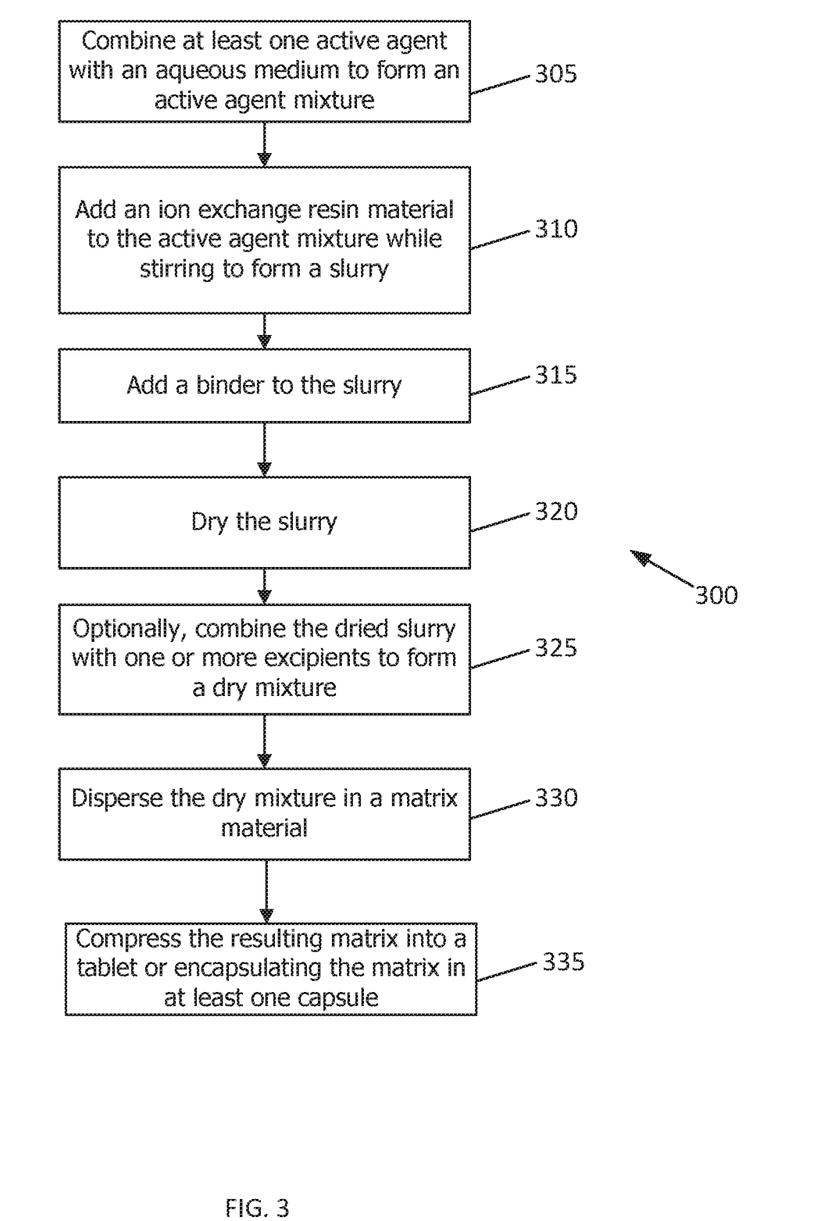
FIG. 3 is a flow chart of an exemplary method for preparing a pharmaceutical composition comprising a complex of at least one active agent and an ion exchange material, according to an exemplary embodiment of the present disclosure.

In at least one embodiment, be at least one active agent is added to the aqueous medium in an amount such that the they form a solution having a concentration of the at least one active agent in the aqueous medium ranging from, as non-limiting examples, about 10 mg/mL, to about 100 mg/mL, from about 20 mg/mL, to about 90 mg/mL, from about 30 mg/mL to about 80 mg/mL, from about 40 mg/mL to about 70 mg/mL, or from about 50 mg/mL to about 60 mg/mL step 305). In at least one embodiment, the concentration of the at least one active agent in the aqueous medium is about 50 mg/mL.

In at least one embodiment, the ion exchange material is added to the at least one active agent in an amount such that the weight ratio of the ion exchange material to the at least one active agent in the mixture (with or without an aqueous medium) ranges, as non-limiting examples, from about 1:1 to about 20:1 or about 1:1 to about 10:1, such as from about 4:1 to about 6:1, or such as from about 3:1 to about 5:1. In at least one embodiment, the ion exchange material and the at least one active agent are combined at a weight ratio chosen from about 2:1, about 3:1, about 4:1, about 5:1, about 6:1, about 7:1, about 8:1, about 9:1, about 10:1, about 11:1, about 12:1, about 13:1, about 14:1, about 15:1, about 16:1, about 17:1, about 18:1, about 19:1, and about 20:1. In at least one embodiment, the weight ratio of ion exchange material to the at least one active agent is about 5:1 when the ion exchange material and the at least one active agent are mixed.

In at least one embodiment, the method comprises letting the aqueous mixture of the at least one active agent, the ion exchange material, and an aqueous medium stand for a period of about 24 hours or less, about 12 hours or less, about 8 hours or less, about 4 hours or less, about 2 hours or less, about 1.5 hours or less, about 1 hour or less, about 50 minutes or less, about 45 minutes or less, about 40 minutes or less, about 30 minutes or less. In at least one embodiment, the standing aqueous mixture is agitated, e.g., by stirring or shaking, for at least a portion of the time, and, in at least some embodiments, all of the time, prior to drying. Accordingly, in at least one embodiment, the aqueous mixture is left to stand, while mixing, for about 2 hours. In at least one embodiment, however, it is not necessary to let the aqueous mixture stand prior to drying.

In at least one embodiment, after combining the at least one active agent, the ion exchange material, and the aqueous medium, the resulting aqueous mixture is dried, as non-limiting examples, via spray drying, top drying, or forced air drying such as in a fluid bed dryer or an oven, or any other suitable drying method known in the art for a period of time ranging, for example, from about 15 minutes to about 12 hours, from about 1 hour to about 4 hours, or from about 1 hour to about 2 hours. In at least one embodiment, the resulting aqueous mixture is dried in a fluid bed dryer for about 1 hour.

In at least one embodiment, after combining the at least one active agent, the ion exchange material, the binder and the aqueous medium, the resulting aqueous mixture is dried, as non-limiting examples, via spray granulation, spray drying, top drying, or forced air drying such as in a fluid bed dryer or an oven, or any other suitable drying method known in the art. The aqueous mixture may be dried for a period of time ranging from for example, about 15 minutes to about 12 hours, from about 1 hour to about 4 hours, or from about 1 hour to about 2 hours. In at least one embodiment, the resulting aqueous mixture is dried in a fluid bed dryer for about 1 hour.

One or more substrates can be incorporated. In at least one non-limiting example, the substrate comprises sugar spheres or particles, and a mixture of the complex of the at least one active agent and the ion exchange material and the binder is mixed with the sugar spheres or particles, thereby forming a complex-substrate granulation or a complex-substrate composition. In at least one other embodiment, the substrate may comprise a second active agent, such as, for example, acetaminophen in granular form, such that the mixing results in a complex-substrate granulation or composition comprising at least two active agents.

In at least one embodiment, the complex-substrate granulation or composition is incorporated into the pharmaceutical composition without washing or rinsing. However, washing and rinsing is not excluded from the scope of the disclosure.

FIG. 3 is a flow chart of an exemplary method 300 for preparing a pharmaceutical composition comprising a complex of an active agent and an ion exchange material according to an exemplary embodiment of the present disclosure. As shown in FIG. 3, method 300 may include combining at least one active agent (such as, for example, oxycodone hydrochloride) and an aqueous medium (such as, for example, water) to form a mixture (step 305) having, for example, a concentration of the at least one active agent in the aqueous medium of about 10 mg/mL to about 200 mg/mL or about 50 mg/mL to about 150 mg/mL, about 75 mg/mL to about 110 mg/mL, or about 110 mg/mL. Method 300 may also include adding an ion exchange material (such as, for example, AMBERLITE® IRP69) to the mixture while stirring to form a slurry or suspension (step 310). Method 300 may further include adding a binder to the slurry or suspension (step 315). Method 300 may further include drying the slurry or suspension, for example, during a spray granulation process, or in a fluid bed dryer for a period of time ranging from, for example, about 15 minutes to about 12 hours, such as, about 2 hours (step 320). Optionally, method 300 may include combining the slurry or suspension having the binder with at least one excipient (step 325), for example, during a spray granulation process to form granules. Method 300 may further include dispersing the slurry or suspension containing the binder and optionally, at least one excipient (e.g., as granules), in a matrix material (step 330). Method 300 may include compressing the resulting dry mixture into tablets or encapsulating the resulting dry mixture in capsules (step 335).

Figure 4:
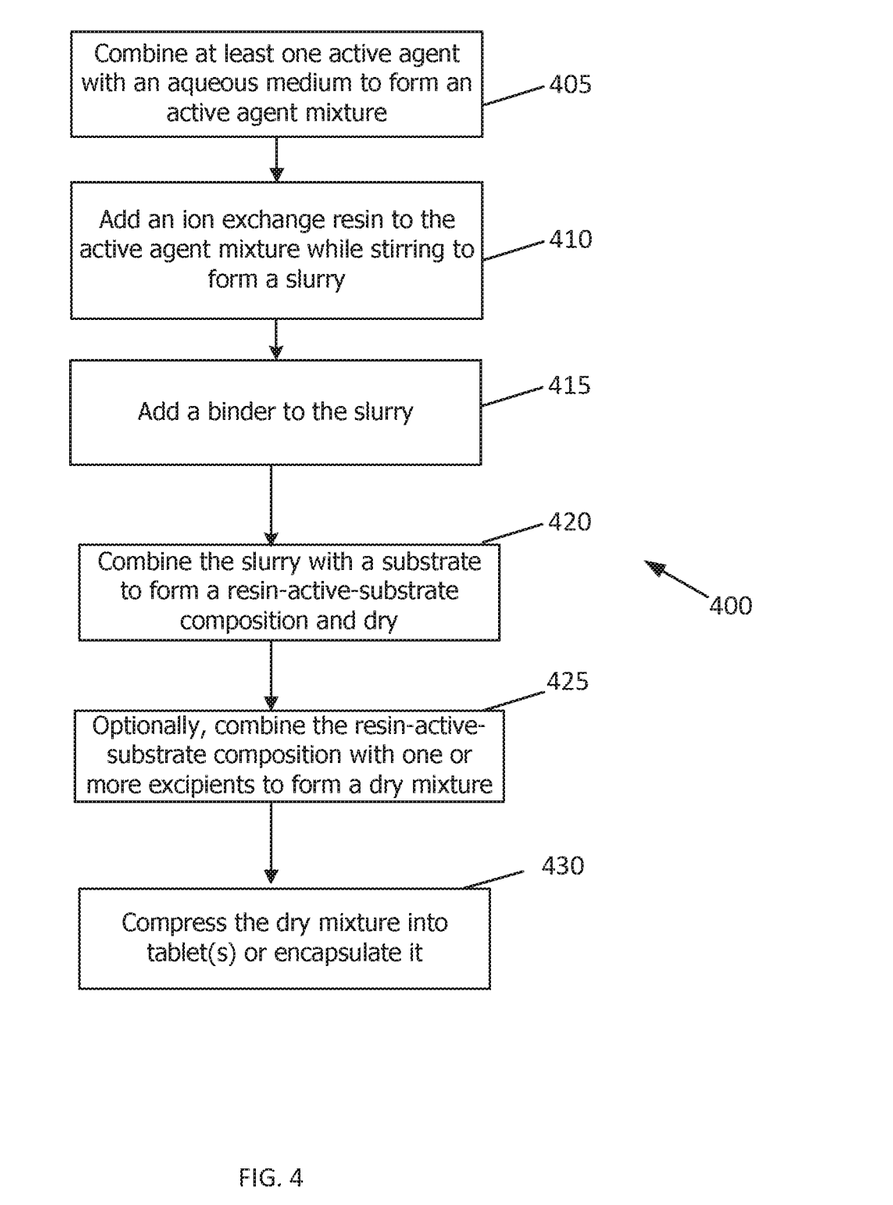
FIG. 4 is a flow chart of an exemplary method for preparing a pharmaceutical composition comprising a complex of at least one active agent and an ion exchange material, according to an exemplary embodiment of the present disclosure.

FIG. 4 is a flow chart of an exemplary method 400 for preparing a pharmaceutical composition comprising a complex of at least one active agent and an ion exchange material, according to an exemplary embodiment of the present disclosure. As shown in FIG. 4, method 400 may include combining at least one active agent (such as, for example, oxycodone hydrochloride) and an aqueous medium (such as, for example, water) to form a mixture (step 405) having, for example, a concentration of the at least one active agent in the aqueous medium of about 10 mg/mL to about 100 mg/mL, or about 50 mg/mL. Method 400 may also include adding an ion exchange material (such as, for example, AMBERLITE® IRP69) to the mixture while stirring to form a slurry or suspension (step 410). Method 400 may further include adding a binder to the slurry (step 415). Method 100 may further include combining the slurry or suspension having the binder with a substrate (such as, for example, particles or granules of a second active agent, sugar spheres, or any other suitable substrate known in the art) and drying (step 420). In at least one embodiment, step 420 may comprise combining the slurry or the suspension and the substrate by spray granulation, spray drying or top spraying the slurry or suspension onto the substrate using a fluid bed dryer for an amount of time suitable to form a dry complex-substrate granulation or composition, wherein the amount of time suitable may range, for example, from about 15 minutes to about 12 hours, from about 1 hour to about 4 hours, or from about 1 hour to about 2 hours. In at least one embodiment of step 420, the slurry or suspension is mixed with the substrate and dried in a fluid bed dryer for about 1 hour to form a complex-substrate composition. Method 400 may optionally include adding at least one excipient to the complex-substrate composition (step 425) and compressing the resulting mixture into tablets or encapsulating the resulting mixture in capsules (step 430).

In at least one embodiment, methods of preparing the pharmaceutical compositions disclosed herein comprise combining the at least one active agent and ion exchange material to form an admixture. In such at least one embodiment, the method comprises mixing the at least one active agent, the ion exchange material, the binder and the matrix material in the absence of an aqueous medium and forming a pharmaceutical composition by, as non-limiting examples, granulating the resulting dry mixture to form granules and either compressing the granules into tablets or filling capsules with the granules using any suitable technique known in the art. In at least one optional embodiment, the admixture of the at least one active agent and ion exchange material may be combined with (1) a substrate comprising an active agent which is the same as or different than the at least one active agent and (2) optional excipients as disclosed herein to form a dry mixture which may be granulated prior to compression into tablets or encapsulation in capsules using any suitable technique known in the art.

Methods of Using

The present disclosure relates to methods of treating pain comprising administering to a patient in need thereof a pharmaceutical composition disclosed herein, such as, for example, a pharmaceutical composition comprising an opioid analgesic, or an opioid analgesic together with acetaminophen or other non-steroidal anti-inflammatory agent, wherein the opioid analgesic forms an admixture or a complex with arm ion exchange material as described herein.

The present disclosure also relates to methods of treating attention deficit disorder (ADHD) comprising administering to a patient in need thereof a pharmaceutical composition disclosed herein, such as, for example, a pharmaceutical composition comprising an admixture or a complex of a central nervous system stimulant and an ion exchange material as described herein.

The present disclosure further relates to methods of deterring abuse of a drug susceptible to abuse (such as, for example, opioid agonists) comprising preparing a pharmaceutical composition disclosed herein, such as, for example, a pharmaceutical composition comprising an admixture or a complex of an opioid agonist and an ion exchange material as described herein.

The following examples illustrate various embodiments of the present disclosure. They are not intended to be construed to limit the claims in any manner whatsoever.

EXAMPLES

Example 1

Exemplary Method for Making Oxycodone HCl Resinate Tablets

Tablet compositions comprising the formulation set forth in Table 1 were prepared according to the general procedure set forth below.

TABLE 1

| item # | Ingredients | Function | mg/Tab | %/Tab | g/batch |
|---|---|---|---|---|---|
| 1 | Oxycodone HCl | API | 60.00 | 8.00 | 84.00 |
| 2 | Amberlite IRP69 | Cation Exchange Resin | 176.50 | 23.53 | 247.10 |
| 3 | Purified Water | Solvent | 0.00 | 0.00 | 755.00 |
| 4 | Pharmacoat 603 | Binder | 12.00 | 1.60 | 16.80 |
| 5 | Lactose Monohydrate | Filler | 150.00 | 20.00 | 210.00 |
| 6 | MCC101 | Filler | 150.00 | 20.00 | 210.00 |
| 7 | Methocel K4M | Rate controlling polymer (Matrix Material) | 192.00 | 25.60 | 268.80 |
| 8 | Mg stearate | Lubricant | 9.50 | 1.27 | 13.30 |
|  | Total |  | 750.00 | 100.00 | 1875.00 |

1. Dissolve oxycodone hydrochloride in water (e.g., purified water) to form, for example, a 60 mg/mL oxycodone hydrochloride/water solution.
2. Form a slurry by adding AMBERLITE® IRP69 resin to the oxycodone hydrochloride/water solution, while stirring, in an amount such that the weight ratio of ion exchange resin to active agent in the resulting slurry is about 3:1. Continue stirring the slurry for at least about 2 hours.
3. Combine the slurry with a birder (e.g., a low molecular sight HPMC).
4. Granulating by top spraying the slurry (i.e., spray granulation) onto a mixture of lactose monohydrate and microcrystalline cellulose using a fluid bed dryer to form a dry complex-substrate granulation or composition containing granules of the oxycodone HCl/resin complex, low molecular weight HPMC, lactose monohydrate and microcrystalline cellulose.
5. Combine the granules from step 4 with high molecular weight HPMC and subsequently mix with magnesium stearate using a lab scale twinshell blender.
6. Compress the resulting blend to form oval tablets using a rotary tablet press to form tablets having an oval shape of 0.3040 in×0.7380 in, each tablet having a total weight of 750 mg, 60 mg oxycodone HCl and a hardness of about 7 kP to about 12 kP.

Example 2

Syringeability of Oxycodone Hydrochloride from Oxycodone HCl 60 mg Resinate Tablets in Aqueous Solvents Resinate tablets in accordance with the pharmaceutical compositions and methods described herein containing 60 mg oxycodone hydrochloride were tested for syringeability of the oxycodone HCl in tap water and saline under both room temperature (i.e., about 20° C.-25° C., or about 21° C.) and elevated temperature (i.e., 95° C.) conditions. To test for syringeability of oxycodone HCl in the tap water, a tablet was crushed using a mortar and pestle and then placed in a container. Ten mL of tap water at room temperature were added to the 20 mL scintillation vial, and the contents mixed by vigorous shaking for about 2 minutes. A syringe having a 21-gauge needle s then inserted into the resulting mixture with a cotton ball being used as a filter and the plunger drawn back by hand for a period of time which did not exceed 5 minutes. The contents inside the syringe were then measured and analyzed using high performance liquid chromatography (HPLC).

This procedure was repeated using saline as the solvent in place of tap water. In addition, for each solvent, the procedure was repeated with the additional of raising the temperature of the contents of the 10 mL container from room temperature to boiling (e.g., 95° C.) before inserting the syringe.

The results of the syringeability studies are set forth in TABLE 2. The "Amt. Aspirated" column lists the volume of total mixture content aspirated or extracted into the syringe. The "% Extracted Oxycodone HCl" column presents the amount of oxycodone HCl present in the syringe (e.g., as measured by HPLC) relative to the total amount of oxycodone HCl originally in the tablet.

TABLE 2

| Solvent | Trial | Amt. Aspirated (mL) | % Extracted Oxycodone HCl |
|---|---|---|---|
| Tap water (room temperature) | 1 | 0 | 0 |
| Tap water (95° C) | 1 | 0 | 0 |
| Saline (room temperature) | 1 | 0 | 0 |
| Saline (95° C) | 1 | <0.5 | 1.62 |
|  | 2 | <0.5 | 2.37 |
|  | 3 | <0.5 | 1.06 |

Example 3

High Volume Solvent Extraction of Oxycodone Hydrochloride from Oxycodone HCl 60 mg Resinate Tablets in Water Resinate tablets in accordance with the pharmaceutical compositions and methods described herein containing 60 mg oxycodone hydrochloride were tested for solvent extraction. In this solvent extraction study, the resinate tablets were mill and placed in a container. One hundred mL of tap water at either room temperature or 95° C. was added to the container. The contents of the container were mixed using a shaker at medium speed for 5 min, 10, min, 20 min, 60 min and 360 min. The contents inside the container were then measured and analyzed using HPLC.

The results of the high volume solvent extraction study is set forth TABLE 3. The "% Amount" column lists the percent of the oxycodone HCl that could be recovered from the tablet containing 60 mg of oxycodone HCl.

TABLE 3

| Sample | Extraction time at RT (min) | % Amount | Extraction time at 95° C. (Min) | % Amount |
|---|---|---|---|---|
| Oxycodone HCl ER tablet, 60 mg | 5 | 11.72% | 5 | 11.51% |
|  | 10 | 16.58% | 10 | 17.13% |
|  | 20 | 20.23% | 20 | 11.48% |
|  | 60 | 20.23% | 60 | 12.18% |
|  | 360 | 13.01% | 360 | 16.00% |

Example 4

Dissolution Profile of Oxycodone HCl Resinate Tablets Containing

Figure 5:
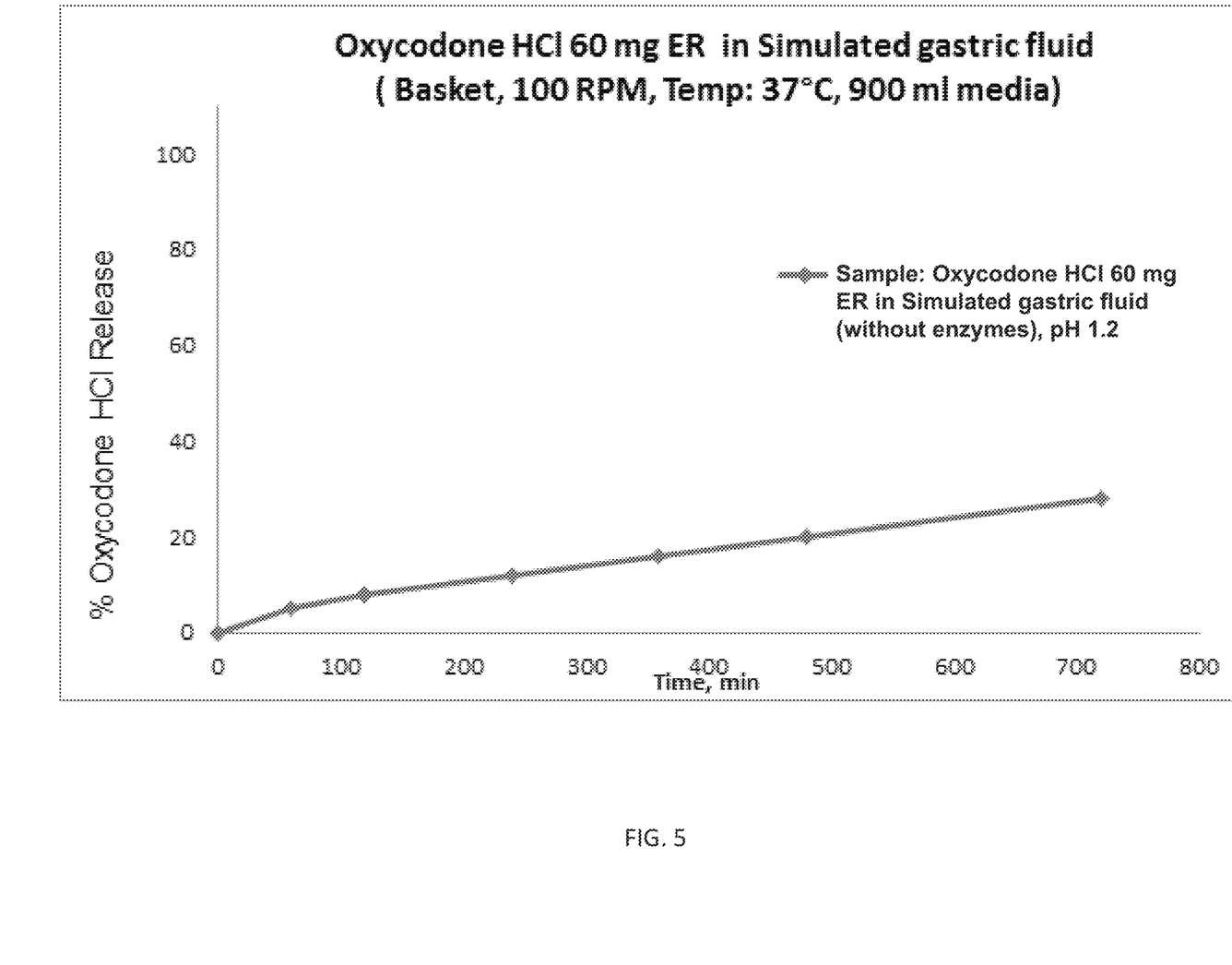
FIG. 5 is a graph presenting the dissolution profile of an exemplary pharmaceutical composition comprising a complex of at least one active agent and an ion exchange material according to an exemplary embodiment of the present disclosure.

Dissolution testing of extended release 60 mg oxycodone HCl resinate tablets prepared as set forth in Example 1, was conducted using a USP apparatus 1 equipped with a horizontal spring across the top of each basket to prevent tablet adhesion, operating at 100 RPM, where the tablets are dissolved in 900 ml of simulated gastric fluid (0.1N HCl) without enzymes. Dissolution data for the tablets is presented in TABLE 4 and the dissolution profile is shown in FIG. 5.

TABLE 4

| Sample Description | % Oxycodone HCl Dissolved | | | | | | |
|---|---|---|---|---|---|---|---|
|  | 0 | 60 | 120 | 240 | 360 | 480 | 720 |
| Rep1 | 0 | 5.35 | 8.37 | 13.23 | 17.31 | 21.24 | 28.85 |
| Rep2 | 0 | 5.05 | 7.85 | 12.32 | 16.27 | 20.03 | 27.32 |
| Rep3 | 0 | 5.03 | 7.74 | 12.18 | 16.13 | 19.84 | 27.06 |
| Rep4 | 0 | 5.00 | 7.66 | 12.04 | 15.99 | 19.68 | 26.91 |
| Rep5 | 0 | 5.26 | 8.03 | 12.59 | 16.6 | 20.58 | 27.99 |
| Rep6 | 0 | 5.17 | 7.89 | 12.47 | 16.43 | 20.17 | 27.44 |
| Min | 0 | 5 | 8 | 13 | 17 | 21 | 29 |
| Max | 0 | 5 | 8 | 12 | 16 | 20 | 27 |
| Average | 0 | 5 | 8 | 12 | 16 | 20 | 28 |
| Rel Std Dev | n/a | 2.7 | 3.2 | 3.4 | 2.9 | 2.8 | 2.6 |

Example 5 (Prophetic)

Dissolution Profile of Oxycodone HCl Resinate Tablets Containing

Extended release 60 mg oxycodone HCl resinate tablets may be prepared substantially as set forth in Example 1, except with less Methocel K4M, or a matrix material having a lower molecular weight than Methocel K4M, and/or with sodium carboxymethyl cellulose as a matrix material. Dissolution testing may be conducted using a USP apparatus 1 equipped with a horizontal spring across the top of each basket to prevent tablet adhesion, operating at 100 RPM, where the tablets are dissolved in 900 ml of simulated gastric fluid (0.1N HCl) without enzymes. The above parameters may be optimized to release about 10% to about 45% active agent after 1 hour, about 12.5% to about 55% (by weight) active agent after 2 hours, about 25% to about 65% (by weight) active agent after 4 hours, about 45% to about 85% (by weight) active agent after 6 hours and about 55% to about 95% (by weight) active agent after 8 hours, and optionally about 75% to 100% (by weight) active agent after 12 hours, when measured by in-vitro dissolution in a USP Apparatus 2 (paddle) at about 50 rpm in about 900 ml simulated gastric fluid at about 37° C.

What is claimed is:

1. A solid oral pharmaceutical composition comprising:
   a mixture comprising:
      an ion exchange resin;
      at least one active agent capable of forming a complex with the ion exchange resin, wherein the at least one active agent comprises a drug susceptible to abuse;
      a binder; and
      a matrix material comprising a polymer having a molecular weight of about 500,000 Da to about 10,000,000 Da,
   wherein the composition, when administered to a patient in need thereof, provides a controlled release of the at least one active agent to the patient with a therapeutic effect for at least about 8 hours,
   wherein the composition releases about 10% to about 45% active agent after 1 hour, about 12.5% to about 55% (by weight) active agent after 2 hours, about 25% to about 65% (by weight) active agent after 4 hours, about 45% to about 85% (by weight) active agent after 6 hours and about 55% to about 95% (by weight) active agent after 8 hours, when measured by in-vitro dissolution in a USP Apparatus 2 (paddle) at about 50 rpm in about 900 ml simulated gastric fluid at about 37° C., and wherein recovery of the at least one active agent is less than about 20% based on a syringeability test whereby the composition is subject to dissolution in 10 ml of water with agitation at room temperature for about 2 min and the resultant solution is aspirated with a 21-gauge needle.

2. The pharmaceutical composition of claim 1, wherein the composition releases about 10% or less of the at least one active agent within about 20 minutes as measured by in-vitro dissolution in a USP Apparatus 2 (paddle) at about 50 rpm in about 900 ml water at about 37° C.

3. The pharmaceutical composition of claim 1, wherein the composition releases about 20% or less of the at least one active agent within about 45 minutes as measured by in-vitro dissolution in a USP Apparatus 2 (paddle) at about 50 rpm in about 900 ml water at about 37° C.

4. The pharmaceutical composition of claim 1, wherein the composition releases about 10% or less of the at least one active agent within about 20 minutes as measured by in vitro dissolution in a USP Apparatus 2 (paddle) at about 50 rpm in about 900 ml 40% ethanol in water v/v at about 37° C.

5. The pharmaceutical composition of claim 1, wherein the composition releases about 20% or less of the at least one active agent within about 45 minutes as measured by in-vitro dissolution in a USP Apparatus 2 (paddle) at about 50 rpm in about 900 ml in 40% ethanol in water v v at about 37° C.

6. The pharmaceutical composition of claim 1, wherein the drug susceptible to abuse is selected from the group consisting of dronabinol, derivatives thereof and mixtures thereof.

7. The pharmaceutical composition of claim 1, wherein the drug susceptible to abuse comprises an opioid agonist.

8. The pharmaceutical composition of claim 7, wherein the opioid agonist is selected from the group consisting of oxycodone, oxymorphone, hydrocodone, hydromorphone, morphine, codeine, tramadol, tapentadol, fentanyl, and pharmaceutically acceptable salts, hydrates and solvates thereof, and mixtures thereof.

9. The pharmaceutical composition of claim 7, wherein the opioid agonist is selected from the group consisting of oxycodone hydrochloride, hydrocodone bitartrate, and hydromorphone hydrochloride.

10. The pharmaceutical composition of claim 7, further comprising at least one second active agent.

11. The pharmaceutical composition of claim 10, wherein the at least one second active agent comprises a non-opioid analgesic.

12. The pharmaceutical composition of claim 11, wherein the non-opioid analgesic is chosen from non-steroidal anti-inflammatory agents and acetaminophen.

13. The pharmaceutical composition of claim 10, wherein the at least one second active agent comprises an antagonist to the active agent.

14. The pharmaceutical composition of claim 13, wherein the antagonist is selected from the group consisting of naltrexone, naloxone, nalmefene, cyclazacine, levallorphan, buprenorphine, pharmaceutically acceptable salts, hydrates and solvates thereof, and mixtures thereof.

15. The pharmaceutical composition of claim 14, wherein the antagonist is selected from the group consisting of naltrexone, naloxone, pharmaceutically acceptable salts, hydrates and solvates thereof, and mixtures thereof.

16. The pharmaceutical composition of claim 14, wherein the antagonist is naltrexone hydrochloride or naloxone hydrochloride.

17. The pharmaceutical composition according to claim 1, wherein the composition comprises a compressed tablet.

18. The pharmaceutical composition according to claim 1, wherein the composition is contained in a pharmaceutically acceptable capsule.

19. The pharmaceutical composition according to claim 1, wherein the weight ratio of the ion exchange resin to the at least one active agent is from about 1:1 to about 10:1.

20. The pharmaceutical composition of claim 1, wherein the mixture is a matrix.

21. The pharmaceutical composition of claim 1, wherein the mixture comprises a complex comprising the at least one active agent and the ion exchange resin.

22. The pharmaceutical composition of claim 1, wherein the binder comprises a low molecular weight polymer.

23. The pharmaceutical composition of claim 1, wherein the matrix material comprises a high molecular weight polymer.

24. The pharmaceutical composition of claim 1, wherein the mixture comprises granules, comprising:
   (a) a complex of the active agent comprising the drug susceptible to abuse and the ion exchange resin; and
       a binder comprising a low molecular weight polymer; and
   (b) the matrix material.

25. The pharmaceutical composition of claim 1, wherein the ion exchange resin is selected from the group consisting of sulfonated copolymer of styrene and divinylbenzene, methacrylic acid-divinylbenzene copolymers and polystyrene resins having amine and/or ammonium side groups.

26. The pharmaceutical composition of claim 1, wherein the binder is selected from the group consisting of a low molecular weight hydroxypropylmethylcellulose, a low molecular weight hydroxypropylcellulose, a low molecular weight hydroxyethylcellulose, polyethylene glycol, an acrylic polymer, an acrylic copolymer, a graft copolymer of polyvinyl alcohol and polyethylene glycol, a polyvinyl alcohol, alginic acid, sodium alginate, starch, pregelatinized starch, sucrose, guar gum, derivatives thereof and combinations thereof.

27. The pharmaceutical composition of claim 1, wherein the matrix material is selected from the group consisting of a high molecular weight hydroxypropylmethylcellulose, a high molecular weight polyethylene oxide, a high molecular weight hydroxyethylcellulose, a high molecular weight hydroxypropylcellulose, a high molecular weight methylcellulose, an alginate, a carbopol, a polymethacrylate, a wax, carnauba wax, beeswax, glycerine alginate and a polyglycolyzed glyceride, and combinations thereof.

* * * * *